(12) United States Patent
Gerber et al.

(10) Patent No.: US 8,801,728 B2
(45) Date of Patent: Aug. 12, 2014

(54) INTRODUCTION OF MEDICAL LEAD INTO PATIENT

(75) Inventors: Martin T. Gerber, Maple Grove, MN (US); Michael D. Baudino, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 504 days.

(21) Appl. No.: 13/011,072

(22) Filed: Jan. 21, 2011

(65) Prior Publication Data

US 2011/0190785 A1 Aug. 4, 2011

Related U.S. Application Data

(60) Provisional application No. 61/299,674, filed on Jan. 29, 2010.

(51) Int. Cl.
*A61B 19/00* (2006.01)

(52) U.S. Cl.
USPC ........... 606/129; 607/128; 607/126; 600/375; 600/381

(58) Field of Classification Search
CPC ............. A61B 17/3468; A61B 19/201; A61N 2001/0578; A61N 2005/1051; A61N 1/05; A61N 1/0502; A61N 1/0504; A61N 1/36; A61N 1/36017; A61N 1/36025; A61N 606/108
USPC ........... 607/115, 116, 45, 134–138, 122–132; 606/129; 600/544, 372–381; 623/1.11
See application file for complete search history.

(56) References Cited

U.S. PATENT DOCUMENTS

| | | | |
|---|---|---|---|
| 4,519,403 A | | 5/1985 | Dickhudt |
| 4,735,205 A | | 4/1988 | Chachques et al. |
| 5,391,200 A | | 2/1995 | KenKnight et al. |
| 5,824,030 A | * | 10/1998 | Yang et al. ............... 607/122 |
| 6,205,361 B1 | | 3/2001 | Kuzma et al. |
| 6,510,347 B2 | * | 1/2003 | Borkan ................... 607/117 |
| 6,512,958 B1 | * | 1/2003 | Swoyer et al. ............ 607/117 |
| 6,522,932 B1 | | 2/2003 | Kuzma et al. |
| 6,606,521 B2 | | 8/2003 | Paspa et al. |
| 7,099,718 B1 | | 8/2006 | Thacker et al. |
| 7,177,702 B2 | | 2/2007 | Wallace et al. |

(Continued)

FOREIGN PATENT DOCUMENTS

| WO | WO98-17345 | 4/1998 |
|---|---|---|
| WO | WO2008-048471 | 4/2008 |

OTHER PUBLICATIONS

U.S. Statutory Invention Registration H1905, Oct. 3, 2000 (Hall).

*Primary Examiner* — Katherine Dowe
*Assistant Examiner* — Sidharth Kapoor

(57) ABSTRACT

Leads having distal electrodes may be used in application of test stimulation for purposes of implanting a lead having a fixation element distal to an electrode array. The fixation element is proximal the distal electrode. Accordingly, the distal electrode may be advanced beyond a distal end of an introducer while the fixation element may be retained in a retracted configuration by the introducer. If the test signals applied by the distal electrode indicate that the distal electrode is in the desired location of the patient, a series of markings on the lead may be used to facilitate placement of the electrode array at the location previously occupied by the distal electrode; i.e. the desired location of the patient. The electrodes of the electrode array may then be used to provide therapy to the patient.

26 Claims, 14 Drawing Sheets

(56) References Cited

U.S. PATENT DOCUMENTS

| | | |
|---|---|---|
| 7,191,018 B2 | 3/2007 | Gielen et al. |
| 7,212,867 B2 | 5/2007 | Van Venrooij et al. |
| 7,376,468 B2 | 5/2008 | King et al. |
| 7,383,090 B2 * | 6/2008 | O'Brien et al. ............... 607/116 |
| 7,684,873 B2 | 3/2010 | Gerber |
| 7,797,054 B2 | 9/2010 | Skubitz et al. |
| 7,856,277 B1 | 12/2010 | Thacker et al. |
| 2002/0065543 A1 * | 5/2002 | Gomperz et al. ............. 607/115 |
| 2002/0147484 A1 * | 10/2002 | Dahl et al. ................... 607/116 |
| 2005/0182390 A1 | 8/2005 | Shanley |
| 2006/0235502 A1 | 10/2006 | Belluche |
| 2007/0050004 A1 * | 3/2007 | Swoyer et al. ................ 607/116 |
| 2007/0162101 A1 | 7/2007 | Burgermeister et al. |
| 2008/0103569 A1 * | 5/2008 | Gerber ......................... 607/115 |
| 2008/0103574 A1 * | 5/2008 | Gerber ......................... 607/116 |
| 2008/0103575 A1 * | 5/2008 | Gerber ......................... 607/117 |
| 2008/0103576 A1 * | 5/2008 | Gerber ......................... 607/128 |
| 2008/0132969 A1 | 6/2008 | Bennett et al. |
| 2009/0043372 A1 | 2/2009 | Northrop et al. |
| 2009/0198252 A1 | 8/2009 | Seifert et al. |
| 2009/0259280 A1 * | 10/2009 | Wilkin et al. ................. 607/116 |
| 2009/0270957 A1 | 10/2009 | Pianca et al. |
| 2010/0069882 A1 | 3/2010 | Jennings |
| 2010/0082086 A1 | 4/2010 | Zhu |

* cited by examiner

INTRODUCTION OF MEDICAL LEAD INTO PATIENT

RELATED APPLICATION

This patent application claims priority to U.S. Provisional Patent Application Ser. No. 61/299,674, filed Jan. 29, 2010, the entire disclosure of which is expressly incorporated herein by reference.

FIELD

The present disclosure relates generally to systems, devices and methods for introducing medical leads into patients, particularly leads having distal fixation elements.

BACKGROUND

A variety of implantable medical devices have been proven to be effective for treatment of a variety of diseases. Many of such devices, such as cardiac pacemakers, defibrillators, spinal cord or deep brain stimulators, gastric stimulators, and the like, employ accessory medical leads to deliver electrical signals from a signal generating device to tissue of a patient at a location removed from the signal generating device. Typically the lead is tunneled from a subcutaneous region of the patient in which the signal generating device is implanted to a target tissue location. It is often important that the lead, or portions thereof, does not shift or move once implanted to ensure that a therapeutic signal continues to be delivered to the target tissue. One mechanism for retaining the implanted position of a lead or portion thereof is the use of tines. The tines or other fixation elements are typically attached to various locations of the lead and are deployed once the lead is properly positioned in the patient. Most often, tines or other fixation elements prevent retrograde movement of the lead. Once the fixation elements are deployed, it can be difficult to change the position of the lead.

Prior to deploying the fixation elements, it is often desirable to apply electrical signals to the patient via electrodes of the lead, as the lead is being implanted, to determine whether the lead is being positioned in an appropriate location or if the tract of implantation is proceeding in a desired direction. This process is sometimes referred to a trolling, where test electrical signals are applied as the lead is advanced to aid in the proper placement of the lead. However, with the use of standard lead introducer devices, it is not possible to perform such trolling when the self-expanding fixation elements are disposed on the lead distal to the electrodes. That is, absent fixation elements being distal electrodes of the lead, the lead may extended distally beyond the introducer (or the introducer may be withdrawn to expose the distal end of the lead) such that a test electrical signal may be delivered to the patient via electrodes of the lead, and the lead may be withdrawn into the introducer (or introducer advanced) and repositioned. This process may be repeated until the lead is determined to be in an appropriate location, and the introducer may be completely withdrawn. However, when the fixation elements are disposed on the lead distal to the electrodes, the fixation elements will be deployed during the initial test stimulation (when extended beyond the distal end of the introducer), and the ability to reposition the lead will be compromised, if not lost.

SUMMARY

This disclosure, among other things, describes systems, devices and methods that allow for trolling to be performed when leads having self-expanding or self-deploying fixation elements, such as tines, distal to electrodes, are implanted. In some embodiments described herein, leads having an electrode, such as a distal tip electrode, more distal than the fixation element is used for purposes of assisting in the determination of whether the distal electrode is in the desired location of a patient. The lead may have a series of markings that aid in allowing the electrode proximal the fixation element to be advanced to the desired location previously occupied by the distal electrode.

In various embodiments, a system includes an introducer and a lead. The introducer has a body member having a proximal end and a distal end. The body member defines a lumen extending from the proximal end to the distal end. The lead is configured to be inserted in the lumen of the introducer. The lead includes a lead body having a proximal end and a distal end, a distal electrode at or near the distal end of the lead body, a fixation element proximal the distal electrode, an electrode array proximal the fixation element, and first and second positional markings. The first positional marking is proximal the electrode array and is positioned a distance from the distal electrode equal to, or greater than, the length of an introducer sheath for use in implanting the lead. The second positional marking is located a distance from the first marking equal to the distance from the distal electrode to a desired location in the electrode array. The second positional marking may be proximal or distal to the first positional marking.

If the second marking is distal to the first positional marking, the distal end of the body member of the introducer may be inserted into the patient and advanced until the distal end is positioned in a location of the patient. The lead may be inserted into the lumen of the introducer until the first marking of the lead is aligned with, or adjacent to, the proximal end of the body member of the introducer, resulting in the distal electrode being extended beyond the distal end of the introducer and the fixation being retained in a retracted position by a portion of the body member of the introducer proximal the distal end. A test electrical signal may be applied to the patient via the distal electrode to determine whether the distal electrode is in a desired location of the patient. If the distal electrode is in the desired location, the introducer body member may be advanced over the lead until the proximal end of the introducer body member is aligned with, or adjacent to, the second marking of the lead. The lead may then be distally advanced through the introducer lumen until the first marking is aligned with, or adjacent to, the proximal end of the introducer. The introducer body member may then be withdrawn over the lead, causing the fixation element to deploy and leaving the lead implanted in the patient such that the desired location of the electrode army is positioned in the desired location of the patient.

If the second marking is proximal to the first positional marking, the distal end of the body member of the introducer may be inserted into the patient and advanced to a location in the patient. The lead may be inserted into the lumen of the introducer until the first marking of the lead is aligned with, or adjacent to, the proximal end of the body member of the introducer, resulting in the distal electrode being extended beyond the distal end of the introducer and the fixation element being retained in a retracted position by a portion of the body member of the introducer proximal the distal end. A test electrical signal may be applied to the patient via the distal electrode to determine whether the distal electrode is in a desired location of the patient. If the distal electrode is in the desired location, the lead may be advanced distally through the introducer until the second marking is aligned with, or adjacent to, the proximal end of the introducer, causing the fixation element to deploy. The introducer body member may then be withdrawn over the lead, leaving the lead implanted in the patient such that the desired location of the electrode array is positioned in the desired location of the patient.

In other embodiments described herein, a conductive member, such as a stylet, having a non-conductive distal end portion (or "dummy" portion) that has a length the same as the length from the distal end of the lead to a desired location of the electrode array (where the lead has a fixation element distal the electrode array) is used in combination with an introducer to identify the proper location for lead placement.

For example, a system as described herein may include an introducer, a lead and a conductive member. The introducer has a body member having a proximal end and a distal end. The body member defines a lumen extending from the proximal end to the distal end. The lead is configured to be inserted in the lumen of the introducer and has a proximal end and a distal end. The lead has a fixation element, an electrode array and a positional marker. The fixation element is distal the electrode array, and the positional marker is located proximal to the distal end of the lead a distance equal to the length of the introducer (measured as the length from the proximal end to distal end of the introducer body member). The conductive member is also configured to be inserted in the lumen of the introducer. The conductive member has a non-conductive distal end portion extending from the distal end a distance equal to the distance from the distal end of the lead to the electrode. The conductive member also has a first positional marking located proximal to the distal end of the conductive member by a distance equal to the length of the introducer body member, and a second positional marking proximal to the first marking by a distance greater than the length of the non-conductive distal end portion.

A lead of such a system may be implanted, for example, as follows. The distal end of the body member of the introducer may be inserted into the patient and advanced to a location of the patient. The conductive member may be inserted into the lumen of the introducer until the second marking of the conductive member is aligned with, or adjacent to, the proximal end of the body member of the introducer, resulting in the non-conductive distal end portion of the conductive member and a portion of the conductive member proximal the non-conductive distal end portion extending from the distal end of the introducer. A test electrical signal may be applied to the patient via the conductive portion of the conductive member extending beyond the distal end of the introducer to determine whether the conductive portion is in a desired location of the patient. If the conductive portion is in a desired location of the patient, the introducer may be advanced over the conductive member until the proximal end of the introducer is aligned with, or adjacent to, the first positional marking of the conductive member. The conductive member may be withdrawn from the lumen of the introducer. The distal end of the lead may then be advanced into the lumen of the introducer until the positional marker of the lead is aligned with or adjacent the proximal end of the introducer. The introducer body member may be withdrawn over the lead, deploying the fixation element and leaving the lead implanted in the patient such that the electrode array is positioned in the desired location of the patient.

One or more embodiments described herein provide one or more advantages over prior leads, introducers, other devices, systems and methods for implanting leads having a fixation element distal to an electrode array. Such advantages will be apparent to those of skilled in the art upon reading the following detailed description.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure.

Figure 1:
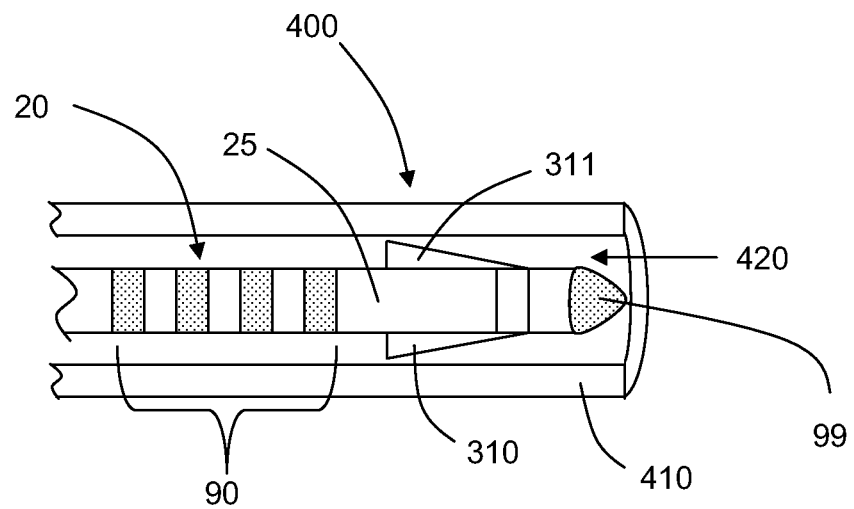
FIGS. 1-2 are schematic sectional views of an introducer having a lead disposed in the lumen of the introducer.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

"Exemplary" or "representative" is used in the sense of "for example" or "for the purpose of illustration", and not in a limiting sense.

As used herein, "providing" in the context of "providing" an article means making, using, or otherwise obtaining the article. For example, providing a lead having certain properties may mean making (including modifying or derivatizing a lead to have such properties), purchasing, using or otherwise obtaining the lead with the certain properties.

In various embodiments, the present disclosure relates to systems, devices and methods related to implanting leads having self-expanding or self-deploying fixation elements distal to electrodes. The fixation elements are associated with (e.g., affixed to or integrally formed with) the implantable medical leads and are configured to anchor the lead within tissue of a patient. Once deployed, the ability to move the lead is compromised or lost. Typically, as a lead is being implanted, test electrical signals are applied to tissue via electrodes of the lead exposed via withdrawal of an introducer sheath. Once the proper lead placement is achieved, as determined by the test signals, the introducer sheath may be fully withdrawn leaving the lead implanted in the desired location. However, when the lead has fixation elements located distal to the electrodes, the introducer sheath may not be withdrawn to apply test stimulation signals because the fixation element would deploy, rendering further movement of the lead difficult at best. Among other things, the present disclosure describes devices, methods and systems that have a distal electrode that allows for test electrical signals to be applied to the patient without deploying the fixation elements and that allow for the electrode proximal the fixation element to be positioned in the location previously occupied by the distal electrode. Once so positioned, the introducer may be withdrawn and the fixation elements deployed, leaving the lead properly positioned in the patient.

Figure 2:
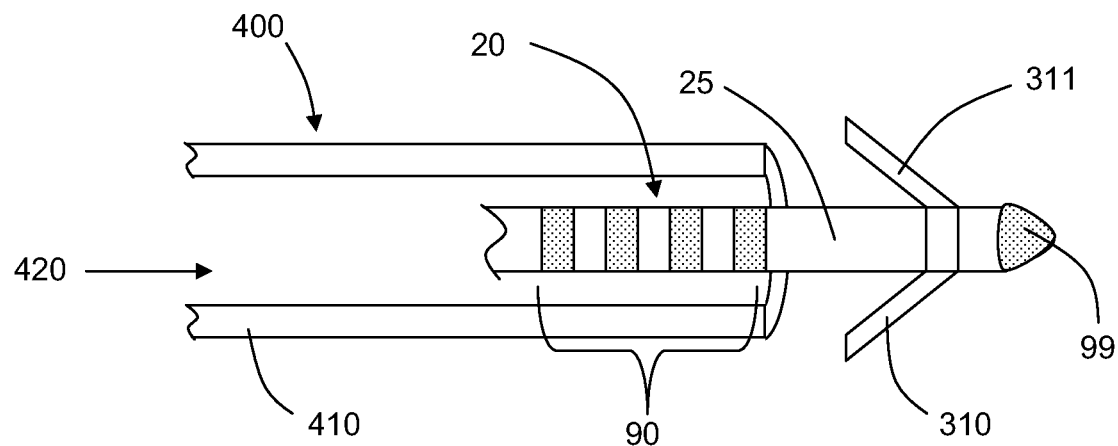

Referring now to FIGS. 1-2, a lead 20 is shown disposed in a lumen 420 of an introducer 400. The introducer 400 includes a body 410 defining the lumen 420. In FIG. 1, the self-expanding or deploying fixation elements 310, 311 (depicted as tines) of the lead 20 are retracted, or deflected proximally, against the lead body 25 by the body 410 of the introducer 400. The fixation elements 310, 311 are located distal the electrode array 90 on the lead 20. The lead 20 has a distal electrode 99 at or near the distal end of the lead. In the depicted embodiment, the distal electrode 99 is a tip electrode. As shown in FIG. 2, when the introducer 400 is withdrawn, or the lead 20 is advanced, such that the electrodes of the electrode array 90 are exposed, the fixation elements 310, 311 deploy. Once the fixation elements 310, 311 are deployed, it is difficult or not practicable to retract the fixation elements 310, 311 and advance the introducer 400 over the lead 20 so that the lead may be repositioned.

Figure 3:
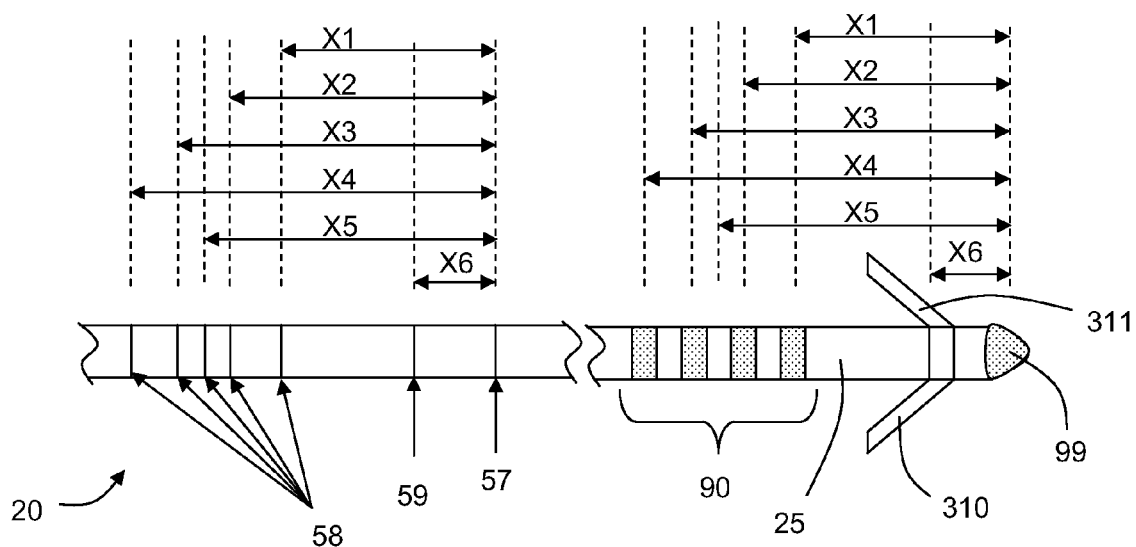
FIG. 3 is a schematic plan view of portions of a lead showing selected distances along the lead.
Figure 4:
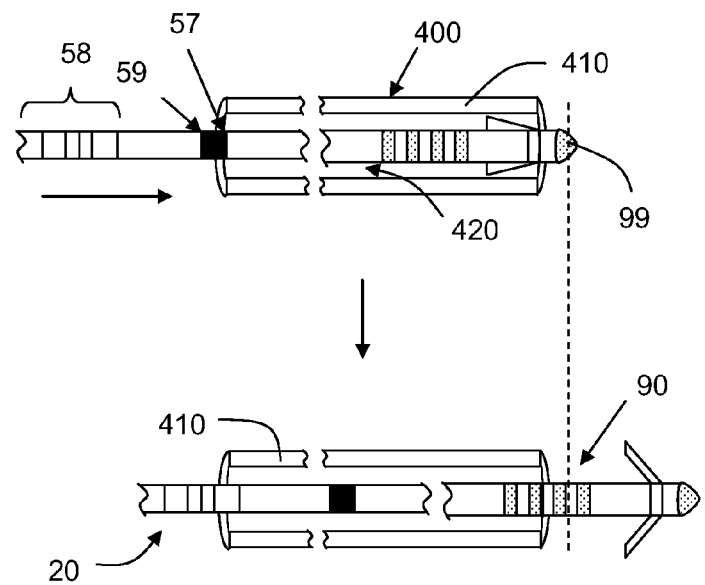
FIG. 4 is a schematic drawing of a method for implanting a lead.

Referring now to FIGS. 3-4, an embodiment of a lead 20 having a distal electrode 99, and fixation elements 310, 311 proximal to the distal electrode 99 and distal to an electrode array 90 is shown. In FIG. 3, embodiments of positional markings 57-58 are shown. In FIG. 4, a schematic overview of how such markings may be used for implanting the lead 20 at a desired location of a patient is depicted.

The lead 20 depicted in FIG. 3 has a first positional marking 57 proximal the electrode array 90. The first marking 57 is positioned a distance from the distal electrode equal to, or greater than, the length of an introducer sheath 400 (see FIG. 4) for use in implanting the lead. Thus, the position of the marking 57 may vary depending on the length of the introducer sheath used. Preferably, the first marking 57 is positioned on the lead 20 at a distance equal to the length of the introducer sheath 400 measured from the proximal end of the distal electrode 99. Thus, when the lead 20 is inserted in the lumen 420 defined by the body member 410 of the introducer 400 such that the first marking 57 is aligned with (or adjacent to) the proximal end of the body member 410 of the introducer, the distal electrode 99 is extended beyond the distal end of the body member 410 of the introducer, allowing for test electrical signals to be applied to a patient via the distal electrode 99.

The lead 20 may include one or more second positional markers 58. The second positional markers 58 are positioned on the lead 20 a distance from the first marking 57 equal to the distance from the distal electrode to a desired location in the electrode array 90. For example, the desired location in the electrode array 90 may be the distance from the distal electrode 99 to a given electrode of the array (e.g. distance X1, X2, X3 or X4, as depicted); the average distance of one or more electrodes of the electrode array 90 from the distal electrode 90 (e.g., distance X5, as depicted, which is the average distance of all of the electrodes of the electrode array 90 from the distal electrode 90), or the like. Thus, as depicted in FIG. 4, the lead 20 may be advanced through the introducer body member 410 until a second marking 58 is aligned with, or adjacent to, the proximal end of the introducer body 410, resulting in the lead advancing in the patient such that the desired portion of the electrode array 90 occupies the space previously occupied by the distal electrode 99. Thus, if the test signal applied by the distal electrode 99 indicates that the distal electrode is positioned in the desired location of the patient, the lead 20 may be advanced through the introducer body 410 until the second marking aligns with (or is adjacent to) the proximal end of the introducer body 410. Then, the desired location of the electrode array 90 should occupy the space previously occupied by the distal electrode 99, and therapy may be delivered to the patient via one or more electrodes of the array 90.

As shown in FIGS. 3-4, the lead 20 may also include a third positional marking 59, which is positioned proximal the first positional marking 57. The third positional marking 59 is located a distance from the proximal end of the fixation elements 310, 311 equal to the length of the introducer. Thus, advancement of the lead 20 in the lumen 420 of the introducer body 410 to a point where the third positional marker 59 of the lead is located distal the proximal end of the introducer body 410 will result in deployment of the fixation elements 310, 311. However, if the lead 20 is not advanced to a point where the third positional marker 59 of the lead is located distal the proximal end of the introducer body 410, the body 410 of the introducer will retain the fixation elements 310, 311 in a retracted configuration. As shown in FIG. 4, the region between the first 57 and third 59 positional markers may be filled in or otherwise indicated to provide a user with a visual cue indicative of the lead 20 being sufficiently advanced in the introducer body 410 to allow for test stimulation by the distal electrode 90 without deployment of the fixation elements 310, 311 (provided that the filled in area is aligned or adjacent with the proximal end of the introducer body 410).

Any suitable marking may be used to form the first 57, second 58, or third 59 markings on or in the body 25 of the lead 20. For example, a biocompatible ink, carbon black, or the like may be incorporated into or on the lead body.

Figure 5:
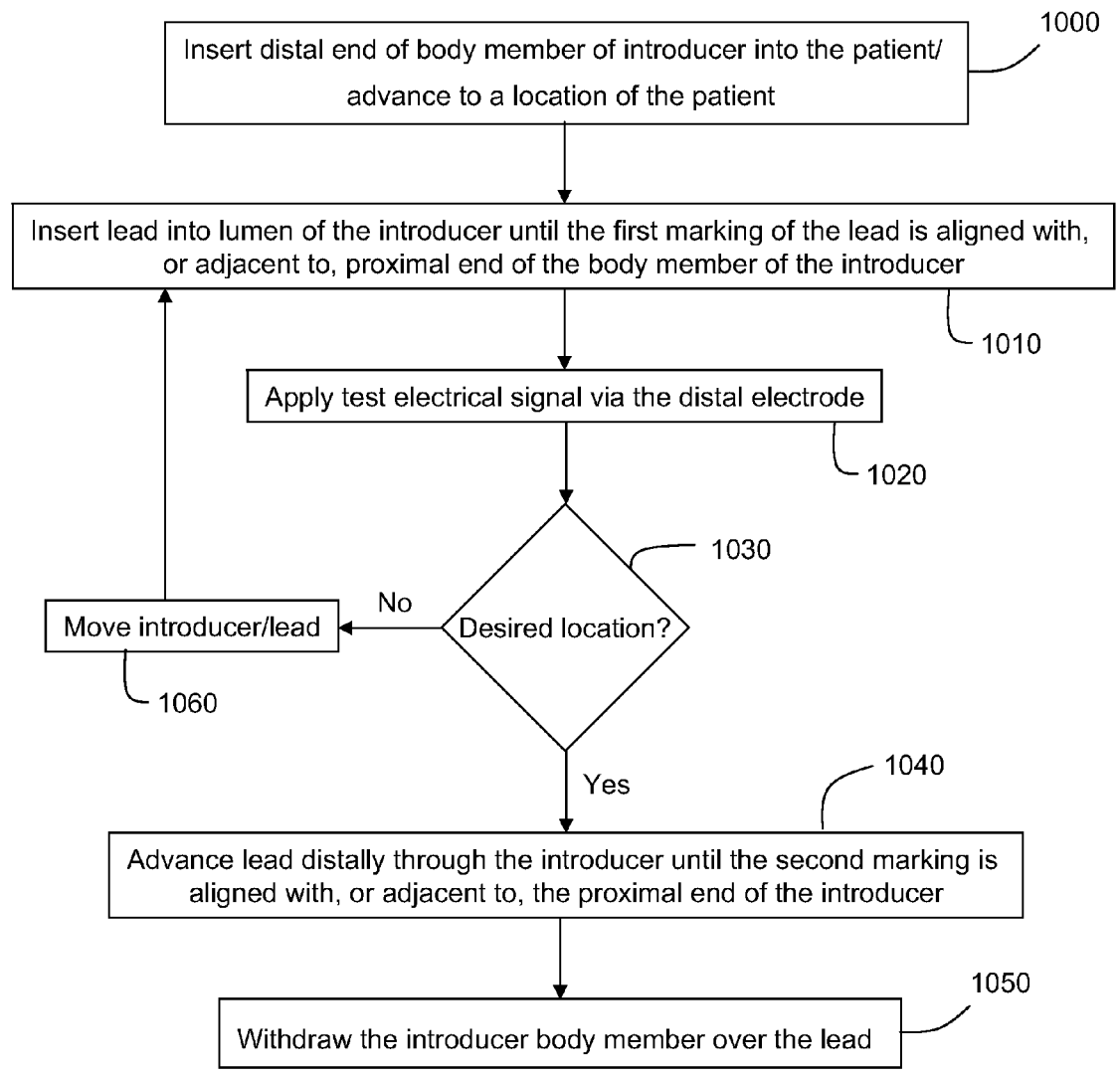
FIG. 5 is a flow diagram of a method for implanting a lead.

Referring now to FIG. 5, a flow diagram depicts an overview of a method similar to that shown schematically in FIG. 4. The method includes inserting the distal end of the body member of the introducer into the patient and advancing the distal end to a location of the patient (1000). A lead is then inserted into the lumen of the introducer until the first marking of the lead is aligned with, or adjacent to, the proximal end of the body member of the introducer (1010), resulting in the distal electrode being extended beyond the distal end of the introducer and the fixation element being retained in a retracted position by a portion of the body member of the introducer proximal the distal end. A test electrical signal may then be applied to the patient via the distal electrode (1020). If it is determined that the distal electrode is in a desired location of the patient based on the test signal (1030), the lead may be advanced distally through the introducer until the second marking is aligned with, or adjacent to, the proximal end of the introducer (1040), causing the fixation elements to deploy. The introducer body member may then be withdrawn over the lead (1050), leaving the lead implanted in the patient such that the desired location of the electrode array is positioned in the desired location of the patient if it is determined that the distal electrode is not in a desired location of the patient based on the test signal (1030), the introducer and lead may be moved (1060) to another location in the patient, and relevant steps repeated until the desired location is identified.

Figure 6:
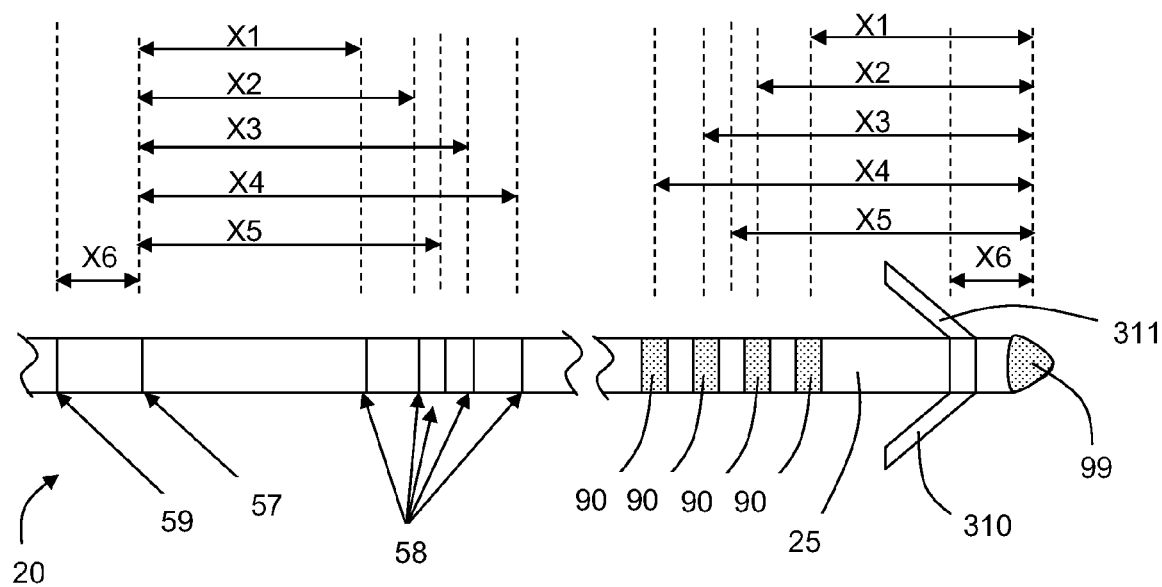
FIG. 6 is a schematic plan view of portions of a lead showing selected distances along the lead.
Figure 7:
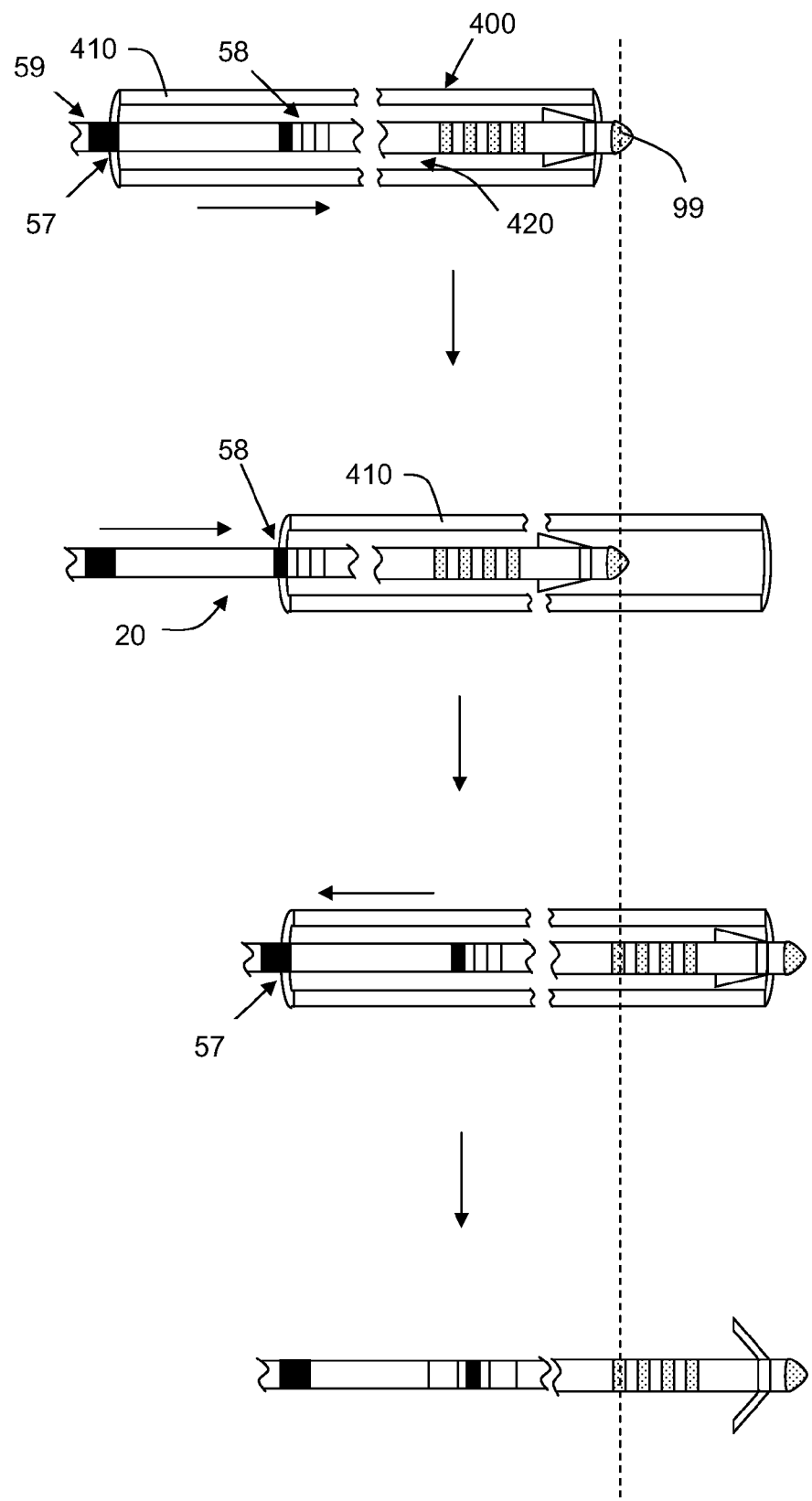
FIG. 7 is schematic drawing of a method for implanting a lead.

The second markings 58 of the lead 20 depicted in FIGS. 3-4 are proximal the first marking 57. However, as depicted in FIGS. 6-7, the second markings 58 of the lead 20 may be distal the first marking 57. In FIG. 6, embodiments of positional markings 57-58 are shown. The markings depicted in FIG. 6 are similar to the markings depicted in FIG. 3, except that the one or more second markings 58 are distal to the first marking 57. Note that the third marking 59 is located proximal to the first marking in both FIGS. 3 and 6. In FIG. 7, a schematic overview of how a lead having markings as depicted in FIG. 6 may be implanted at a desired location of a patient is depicted.

As with the lead depicted in FIG. 3, the lead 20 depicted in FIG. 6 has a first positional marking 57 proximal the electrode array 90. The first marking 57 is positioned a distance from the distal electrode equal to, or greater than, the length of an introducer sheath 400 (see FIG. 7) for use in implanting the lead. Thus, the position of the marking 57 may vary depending on the length of the introducer sheath used. Preferably, the first marking 57 is positioned on the lead 20 at a distance equal to the length of the introducer sheath 400 measured from the proximal end of the distal electrode 99. Thus, when the lead 20 is inserted in the lumen 420 defined by the body member 410 of the introducer 400 such that the first marking 57 is aligned with (or adjacent to) the proximal end of the body member 410 of the introducer, the distal electrode 99 is extended beyond the distal end of the body member 410 of the introducer, allowing for test electrical signals to be applied to a patient via the distal electrode 99.

If the distal electrode 99 is in a desired location, the introducer body 410 may be advanced over the lead 20 until one of the second markers 58 is aligned with or adjacent to the proximal end of the body 410 of the introducer (see, second panel of FIG. 7). The lead 20 may then be advanced in the lumen 420 of the introducer until the first marking 57 is aligned with or adjacent to the proximal end of the body 410 of the introducer (see, third panel of FIG. 7). The introducer body 410 may then be withdrawn over the lead 20, leaving the desired location of the electrode array 90 in the desired location of the patient, which was previously occupied by the distal electrode 99.

The leads and methods depicted in FIGS. 6-7 may be desirable in situations where it may be difficult to advance the lead through tissue of the patient. That is, the introducer body 410 may be advanced and the lead 20 advanced through the introducer rather than the tissue. While not shown, it will be understood that a lead may have second markings 58 both proximal and distal to the first marking 57. Thus, if the lead may be suitably advanced through the tissue, the proximal second markings may be used and the method depicted in, e.g., FIG. 4, may be employed. If the lead cannot be adequately advanced through the tissue, the distal second markings may be employed and the method depicted in, e.g., FIG. 7, may be employed.

Figure 8:
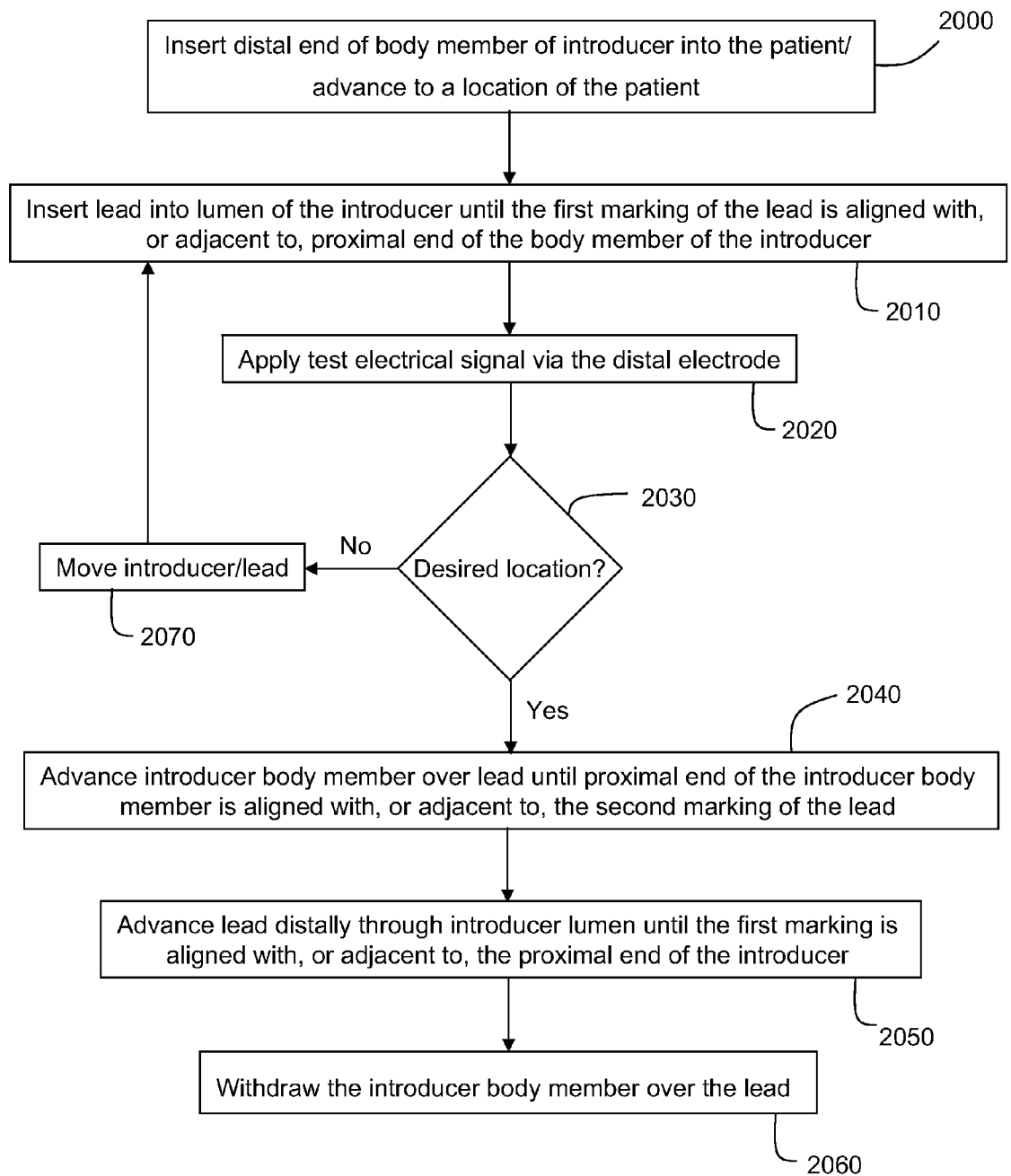
FIG. 8 is a flow diagram of a method for implanting a lead.

Referring now to FIG. 8, a flow diagram depicts an overview of a method similar to that shown schematically in FIG. 7 (where the second markings are distal the first marking). The method includes inserting the distal end of the body member of the introducer into the patient and advancing the distal end to a location of the patient (2000). A lead is then inserted into the lumen of the introducer until the first marking of the lead is aligned with, or adjacent to, the proximal end of the body member of the introducer (2010), resulting in the distal electrode being extended beyond the distal end of the introducer and the fixation element being retained in a retracted position by a portion of the body member of the introducer proximal the distal end. A test electrical signal may then be applied to the patient via the distal electrode (2020). If it is determined that the distal electrode is in a desired location of the patient based on the test signal (2030), the introducer body member may be advanced over the lead until the proximal end of the introducer body member is aligned with, or adjacent to, the second marking of the lead (2040). The lead is then advanced distally through the introducer lumen until the first marking is aligned with, or adjacent to, the proximal end of the introducer (2050). The introducer body member may then be withdrawn over the lead (2060), causing the fixation element to deploy and leaving the lead implanted in the patient such that the desired location of the electrode array is positioned in the desired location of the patient. If it is determined that the distal electrode is not in a desired location of the patient based on the test signal (2030), the introducer and lead may be moved (2070) to another location in the patient, and relevant steps repeated until the desired location is identified.

A lead 20 having a distal electrode 99 as depicted in FIGS. 3, 4, 6, and 7 may be made in accordance with well known processes for manufacturing leads. For example, a percutaneous lead having proximal contacts electrically coupled to distal electrodes may be modified to include a distal electrode. The distal electrode may be a ring electrode or a tip electrode, or the like. A tip electrode may be incorporated into a lead in a manner similar to a ring electrode, except that it has a tip shape. The tip electrode could be solid or hollow and may contain a slot for welding of a connector.

Figure 9:
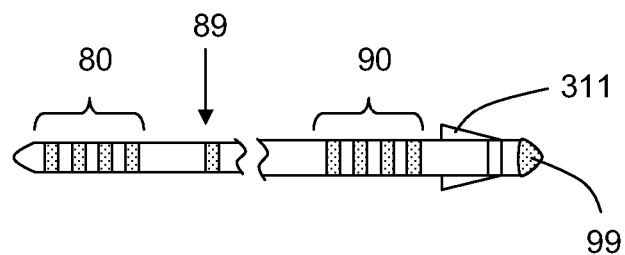
FIGS. 9-10 are schematic plan views of portions of representative leads.
Figure 10:
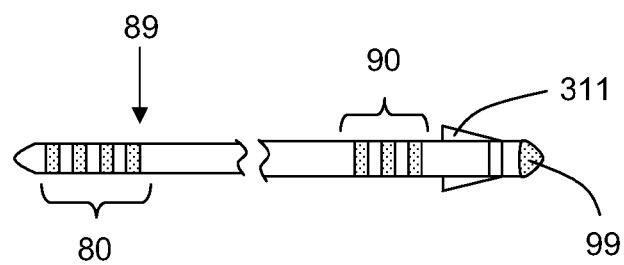
Figure 11:
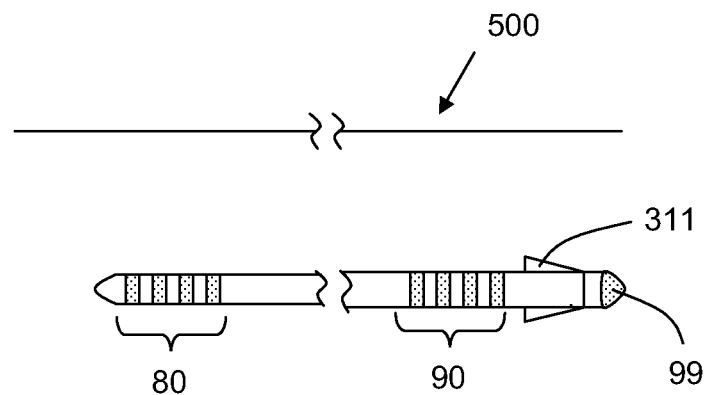
FIG. 11 is a schematic plan view of portions of a representative lead and stylet.
Figure 12:
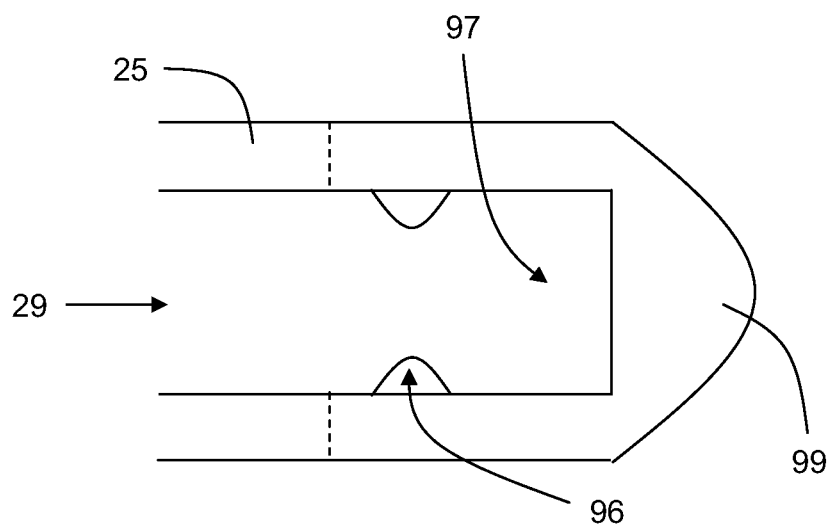
FIGS. 12-14 are schematic sectional views of embodiments of leads having distal electrodes and stylets.
Figure 13:
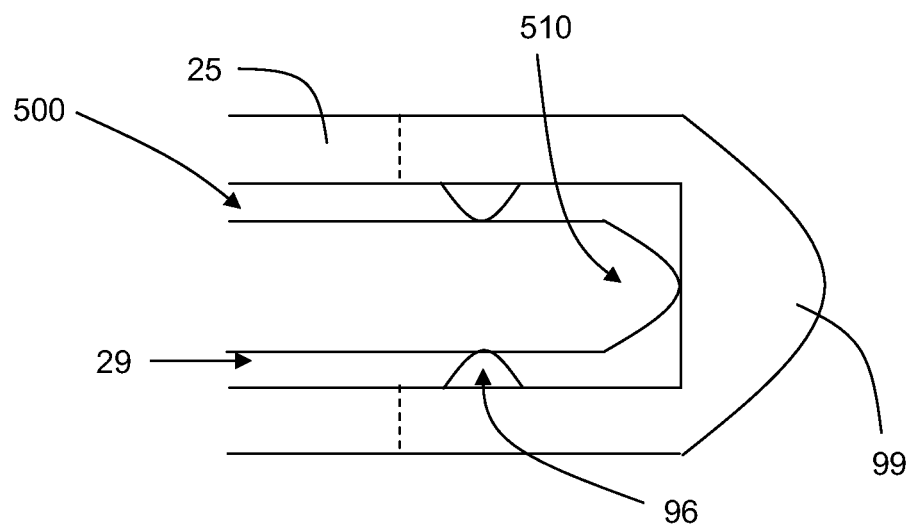
Figure 14:
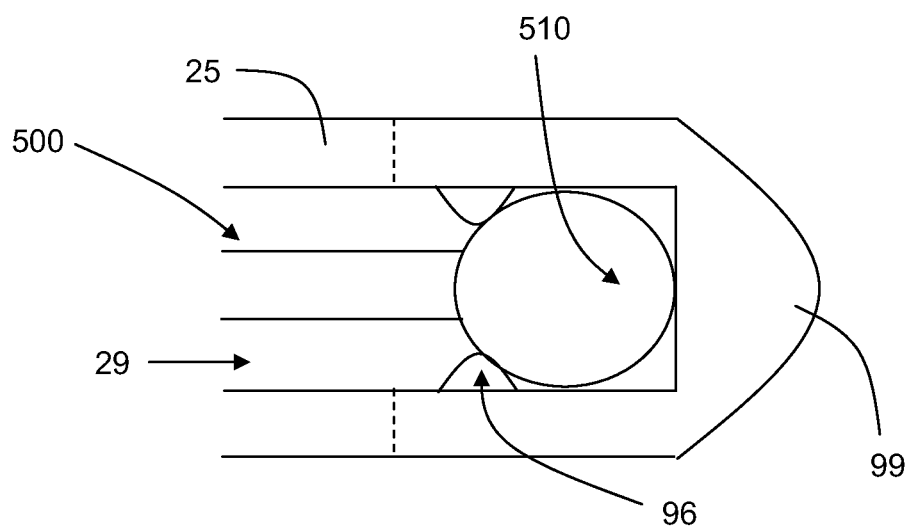

Examples of some lead configurations that may be employed to allow for application of test stimulation pulses via the distal electrode are shown in FIGS. 9-11. The lead 20 depicted in FIG. 9 includes an array of electrodes 90 and an array of contacts 80. Each contact in the array of contacts 80 is electrically coupled to a discrete electrode in the array of electrodes 90 via conductors (not shown) running through the lead body 25 or a lumen (not shown) thereof. Similarly, first contact 89 is electrically coupled to distal electrode 99 via a conductor (not shown) running through the lead body 25 or a lumen (not shown) thereof. In FIG. 9, the first contact 89 coupled to the distal electrode 99 is spaced apart from the array of contacts 80, such that the contact 89 will not be coupled to an implantable medical device, such as a signal generator or lead extension (see, e.g., FIG. 17), when the proximal end of the lead is inserted into a receptacle of the device and the contacts of the array 80 are coupled with the device. Thus, the distal electrode 99 is used only for test stimulation during the implant procedure. The first contact 89 may be configured to be inserted into and coupled with a contact of, for example, an external screener signal generator.

In contrast to the lead depicted in FIG. 9, the corresponding first contact 89 of the lead depicted in FIG. 10 is a part of the array of contacts 80 and is configured to be operably coupled with an implantable medical device when the proximal end of the lead is inserted into a receptacle of the device. Thus, the distal electrode 99 may be used, not only for purposes of applying test signals during the implant procedure, but also for purposes of delivering therapy, if desired, following implantation of the lead. However, the location of the distal electrode 99 may not be optimal for many therapies, and it may be desirable to not employ the distal electrode 99 during therapy delivery in such situations.

Referring now to FIGS. 11-14, embodiments of a lead 20 having a distal electrode 99 that may be electrically coupled with a stylet 500 or other conductive member inserted into a lumen 29 defined by the lead body 25 are depicted. The stylet 500 may also be used to assist in pushing to the lead through an introducer or through tissue of a patient. In the embodiments depicted in FIGS. 12-14, the distal electrode 99 forms a cavity 97 into which deflectable conductive elements 96 project. The deflectable conductive elements 96 have a deflected configuration and an undeflected configuration and are biased toward the undeflected configuration. When the stylet 500 is received in the cavity 97, the deflectable conductive elements 96 assume the deflected configuration, exerting a force on the stylet 500 and form an electrical connection with stylet 500. Thus, the deflectable conductive elements 96 electrically couple the stylet 500 to the distal electrode 99.

The deflectable conductive elements 96 may be formed of any suitable conductive material, such as a shape-memory alloy, a balseal, a canted spring, or the like.

The stylet 500 may have a fairly uniform outer dimension (FIG. 13) or may have a distal feature 510 (FIG. 14) configured to assist in forming electrical contact with the distal electrode 99. In the embodiment shown in FIG. 14, the distal feature 510 and the deflectable contacts 96 may be configured to provide a snap fit of the distal feature 510 in the cavity 97 when the stylet 500 is pushed distally in the lumen 29 of the lead. However, the removal force of the stylet distal feature 510 from the cavity 97 should be relatively low so that removal of the stylet 500 from the lumen 29 of the lead does not result in excessive or undesirable movement of the lead. In some embodiments, the stylet may include an hour glass shaped feature (not shown) that could interlock with a complementary feature of the lead.

Test electrical signals may be applied to a proximal portion of the stylet 500 and transmitted to the distal electrode 99 via the deflectable conductive elements 96 for purposes of determining whether the distal electrode 99 is in a desired location of the patient (e.g., as described above with regard to FIGS. 4, 5, 7 and 8).

Figure 15:
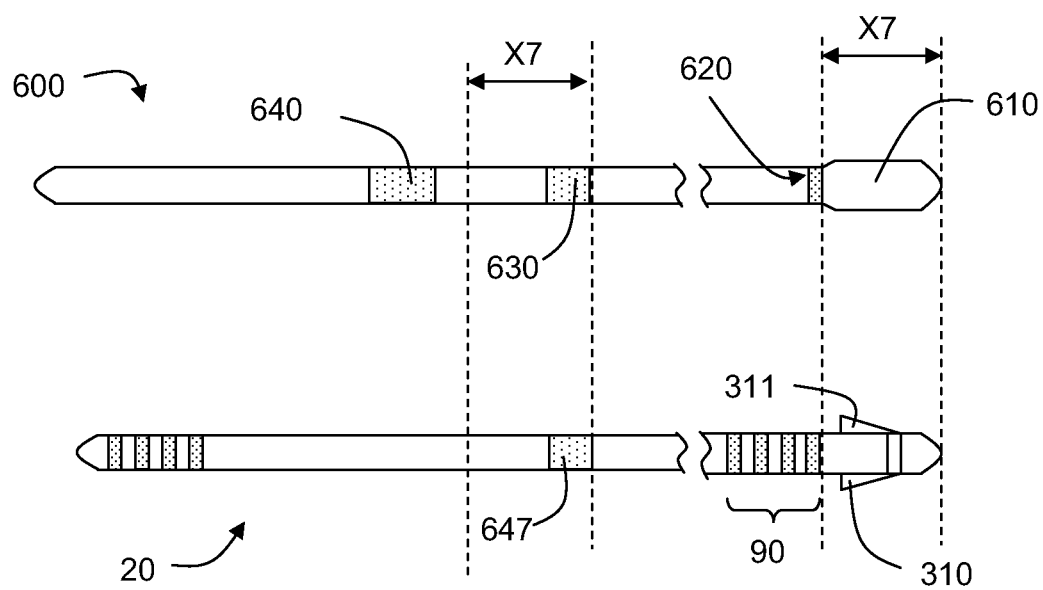
FIG. 15 is a schematic plan view of a conductive member and a lead.

Referring now to FIG. 15, a conductive member 600 that may be used in a process for implanting a lead having fixation elements 310, 311 distal to and array of electrodes 90 is shown. The conductive member has a non-conductive distal end portion 610 extending from the distal end a distance equal to the distance from the distal end of the lead to a desired location in the electrode array 90. The desired location may be, for example, the distance (X7) from the distal end of lead to an electrode of the array 90, the average distance from the distal end of the lead to of one or more electrodes of the electrode array 90, or the like. Proximal the non-conductive distal end portion 610, the conductive member 600 includes a conductive element 620, such as an electrode. In some embodiments, a conductive element is part of a conductive body of the conductive member 600, where the distal end portion 610 is an insulated portion. For example, the conductive member 600 may be formed from a metallic bar, such as a stylet, and the distal end portion 610 may be coated or bonded with a non-conductive polymer. In such embodiments, the entire uninsulated portion of the conductive member would be the conductive element 620. However, it will be understood that any suitable structure, including a device having an electrode, will be useful in assisting placement of a lead 20 having fixation elements 310, 311 distal to an electrode array 90, as described below with regard to FIG. 16.

The conductive member may have positional markings, such as first 630 and second 640 markings. In the embodiment depicted in FIG. 15, the first positional marking 630 is located proximal the distal end of the conductive member by a distance equal to the length of the introducer body member that will be used for inserting the lead 20 and the conductive member 600, as will be described in more detail below with regard to FIG. 16. The conductive member may also include a second positional marking 640 proximal the first marking 630 by a distance greater than the length of the non-conductive distal end portion.

The lead 20, which does not have an electrode distal the fixation elements 310, 311 in this illustrated embodiment, also may have a positional marking 647 that is located at a distance from the distal end of the lead equal to the length of the introducer to be used. Thus, the first positional marking 630 of the conductive member 600 and the positional marking 647 on the lead 20 may be aligned.

Figure 16:
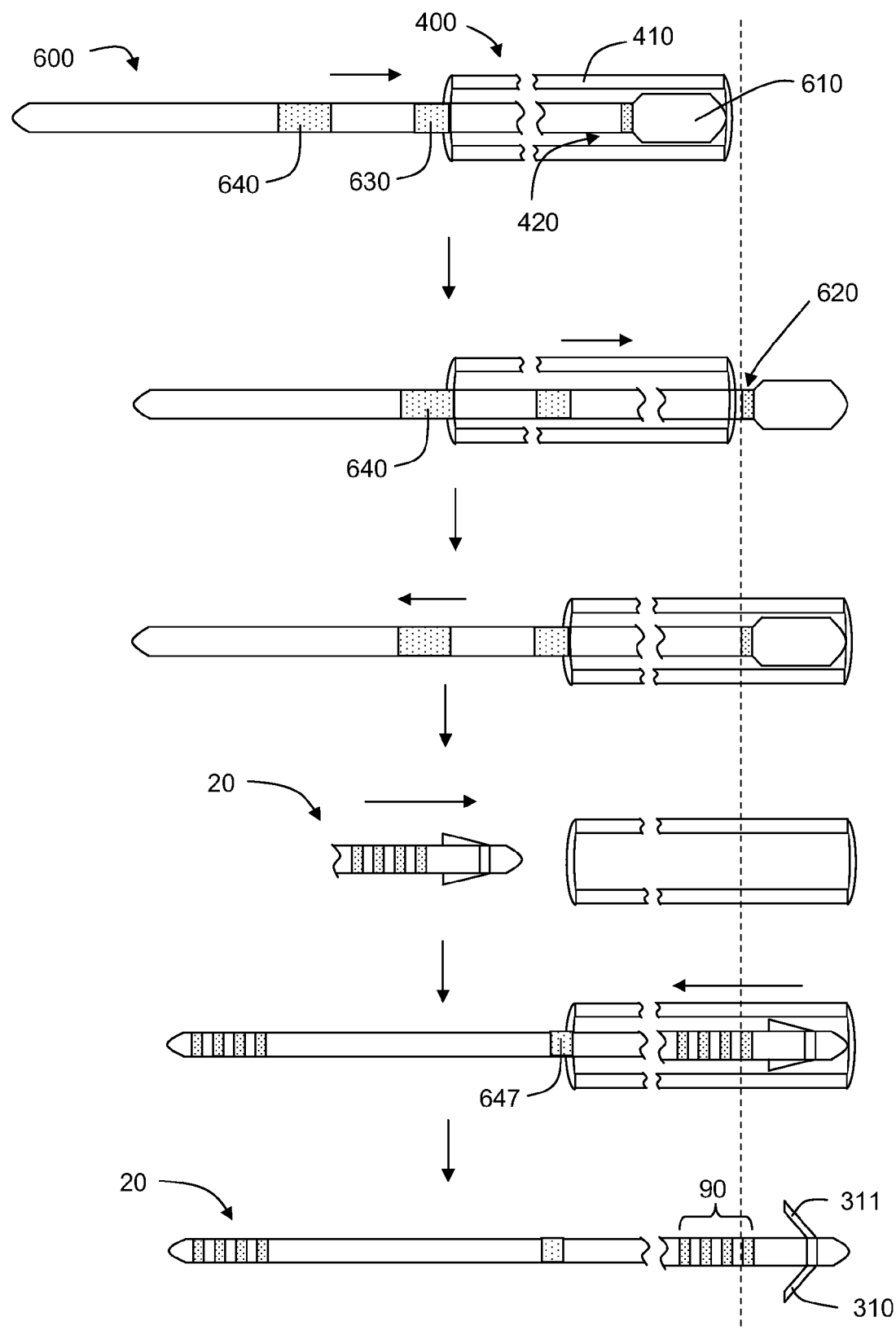
FIG. 16 is a schematic drawing of a method for implanting a lead using a conductive member.

Referring now to FIG. 16, a method for implanting a lead 20 having fixation elements distal an electrode array using a conductive member 600 as described with regard to FIG. 15 is shown in schematic drawings. The method includes inserting the distal end of the body member 410 of the introducer 400 into the patient, advancing the distal end to a location of the patient, and inserting a conductive member 600 into the lumen 420 of the introducer (see top panel). The conductive member 600 is advanced until the second marking 640 of the conductive member 600 is aligned with, or adjacent to, the proximal end of the body member 410 of the introducer, resulting in the non-conductive distal end portion 610 of the conductive member and at least a portion of the conductive member proximal the non-conductive distal end portion extending from the distal end of the introducer 400. Thus, a conductive element 620 or a conductive portion of the conductive member 600 extends beyond the distal end of the body 410 of the introducer (see second panel). A test signal may be applied to the to the patient via the conductive portion 620 of the conductive member 600 extending beyond the distal end of the introducer body 410 to determine whether the conductive portion 620 is in a desired location of the patient. If the conductive portion is in a desired location of the patient, the introducer body 410 may be advanced over the conductive member 600 until the proximal end of the introducer body member is aligned with, or adjacent to, the first positional marking 630 of the conductive member 630 (see third panel). The conductive member 600 may be withdrawn from the lumen 420 of the introducer, and the distal end of the lead 20 may be advanced into the lumen 420 of the introducer (see fourth panel). The lead 20 is advanced until the positional marker 647 is aligned with or adjacent the proximal end of the introducer body 410 (see fifth panel). The introducer body 410 may be withdrawn over the lead 20, deploying the fixation elements 310, 311, and leaving the lead 20 implanted in the patient such that the desired location of the electrode array 90 is positioned in the desired location of the patient (see bottom panel).

It will be understood that the leads, introducers, other devices, systems and methods described herein may be used to implant a lead having a fixation element distal to an electrode array for any suitable purpose. A general overview of systems that may employ such leads is provided in FIGS. 17-19. For the purpose of convenience, the fixation element(s) distal the electrodes are not shown in FIGS. 17-19.

Figure 17:
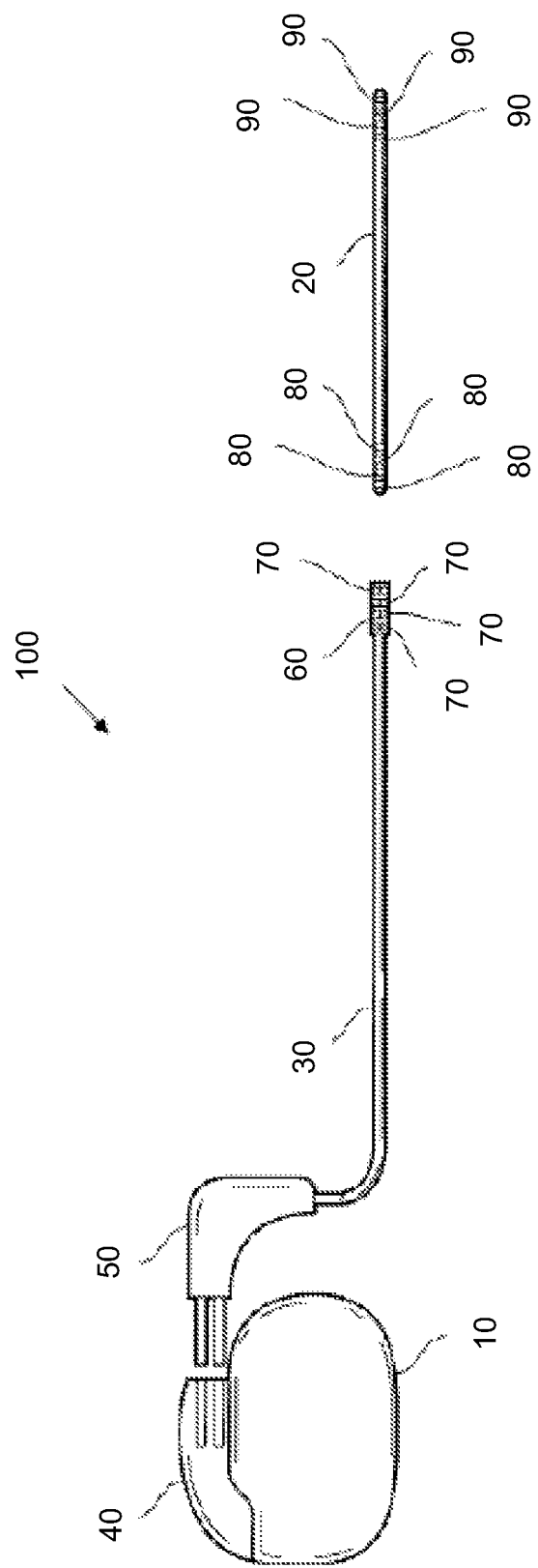
FIG. 17 is a schematic view of a representative implantable electrical signal therapy system.

Referring to FIG. 17, a schematic exploded view of a representative implantable active electrical system 100 is shown. In the system shown in FIG. 17, implantable active electrical device 10 comprises a connector header 40 configured to receive connector 50 at the proximal end of lead extension 30. Of course, it will be understood that device 10 need not have a separate header 40 to receive extension 30. The distal end of extension 30 includes a connector 60 configured to receive the proximal end of lead 20. Connector 60 has internal electrical contacts 70 configured to electrically couple extension 30 to lead 20 via electrical contacts 80 disposed on the proximal end portion of lead 20. Electrodes 90 are disposed on the distal end portion of lead 20 and are electrically coupled to electrical contacts 80, typically through conductors (not shown). Lead 20 may include any number of electrodes 90, e.g. one, two, three, four, five, six, seven, eight, sixteen, thirty-two, or sixty-four. Typically, each electrode 90 is electrically coupled to a discrete electrical contact 80. While not shown, it will be understood that lead 20 may be directly coupled to active implantable medical device 10 without use of extension 30 or adaptor in some systems 100.

Any suitable active implantable medical device employing leads for transmission or receipt of electrical signals may be employed in accordance with the teachings presented herein. For example, a lead may be associated with an active implantable medical device, such as a hearing implant; a cochlear implant; a sensing or monitoring device; a signal generator such as a cardiac pacemaker or defibrillator, a neurostimulator (such as a spinal cord stimulator, a brain or deep brain stimulator, a peripheral nerve stimulator, a vagal nerve stimulator, an occipital nerve stimulator, a subcutaneous stimulator, etc.), a gastric stimulator; or the like.

Figure 18:
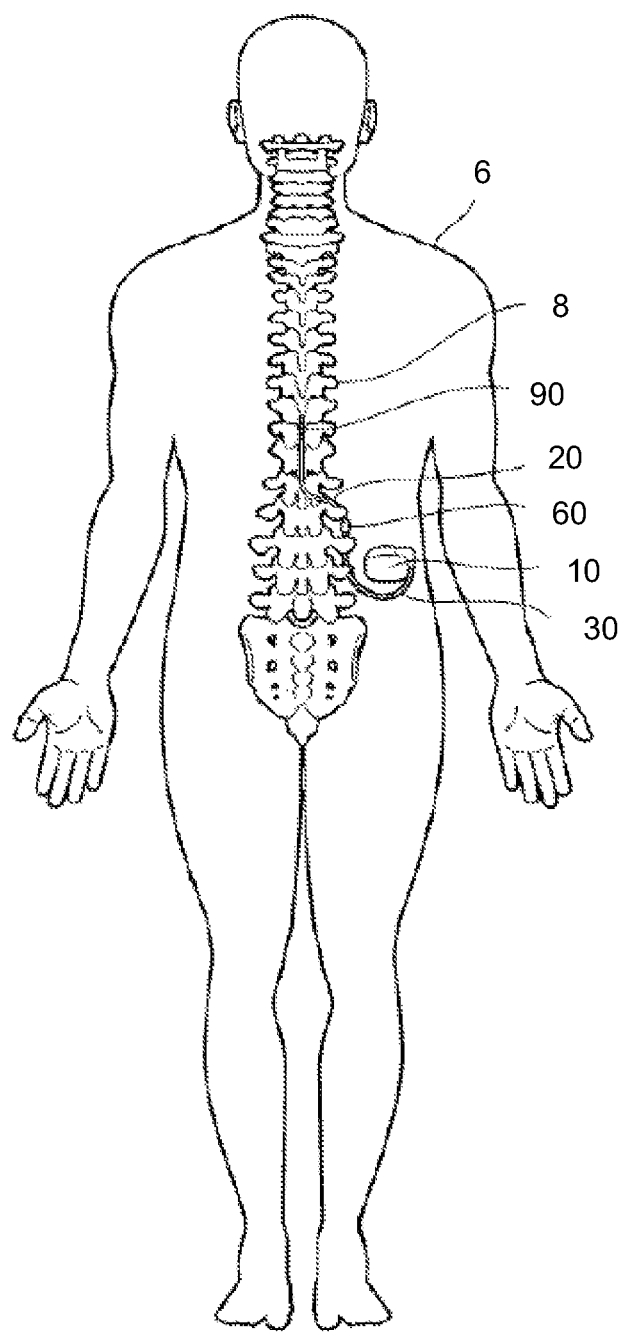
FIG. 18 is a schematic representation of an exemplary spinal cord stimulation (SCS) system implanted in a patient.

By way of example and referring to FIG. 18, a spinal cord stimulation (SCS) system is shown implanted in a patient 6. For SCS, an implantable pulse generator (IPG) 10 is typically placed in the abdominal region of patient 6 and lead 20 is placed at a desired location along spinal cord 8. Such a system, or any system including an IPG 10 as described herein, may also include a programmer (not shown), such as a physician programmer or a patient programmer. IPG 10 is capable of generating electrical signals that may be applied to tissue of patient 6 via electrodes 90 for therapeutic or diagnostic purposes. IPG 10 contains a power source and electronics for sending electrical signals to the spinal cord 8 via electrodes 90 to provide a desired therapeutic effect.

Figure 19:
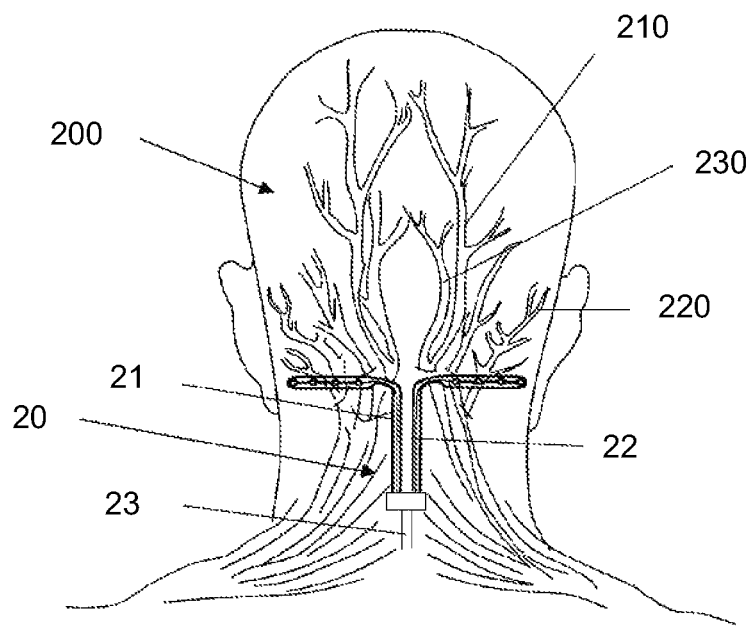
FIG. 19 is a schematic representation of an exemplary bifurcated lead implanted in a patient.

By way of further example and referring to FIG. 19, lead 20 is shown implanted in a patient to provide bilateral therapy to left and right occipital nerves 200. Lead 20 is bifurcated and includes first 21 and second 22 branches forming from a proximal stem portion 23. Of course, two separate leads or lead. extensions may be employed for providing electrical signals to occipital nerves 200. As used herein, occipital nerve 200 includes the greater occipital nerve 210, the lesser occipital nerve 220 and the third occipital nerve 230. The greater and lesser occipital nerves are spinal nerves arising between the second and third cervical vertebrae (not shown). The third occipital nerve arises between the third and fourth cervical vertebrae. The portion of the occipital nerve 200 to which an electrical signal is to be applied may vary depending on the disease to be treated and associated symptoms or the stimulation parameters to be applied. In various embodiments, the lead distal portions that contain electrodes are placed to allow bilateral application of electrical signals to the occipital nerve 200 at a level of about C1 to about C2 or at a level in proximity to the base of the skull. The position of the electrode(s) may vary. In various embodiments, one or more electrodes are placed between about 1 cm and about 8 cm from the midline to effectively provide an electrical signal to the occipital nerve 200.

Application of electrical signals to an occipital nerve for treatment of headache, such as migraine, is one particular example or where it may be desirable to employ a lead having a fixation element distal the electrodes.

Figure 20:
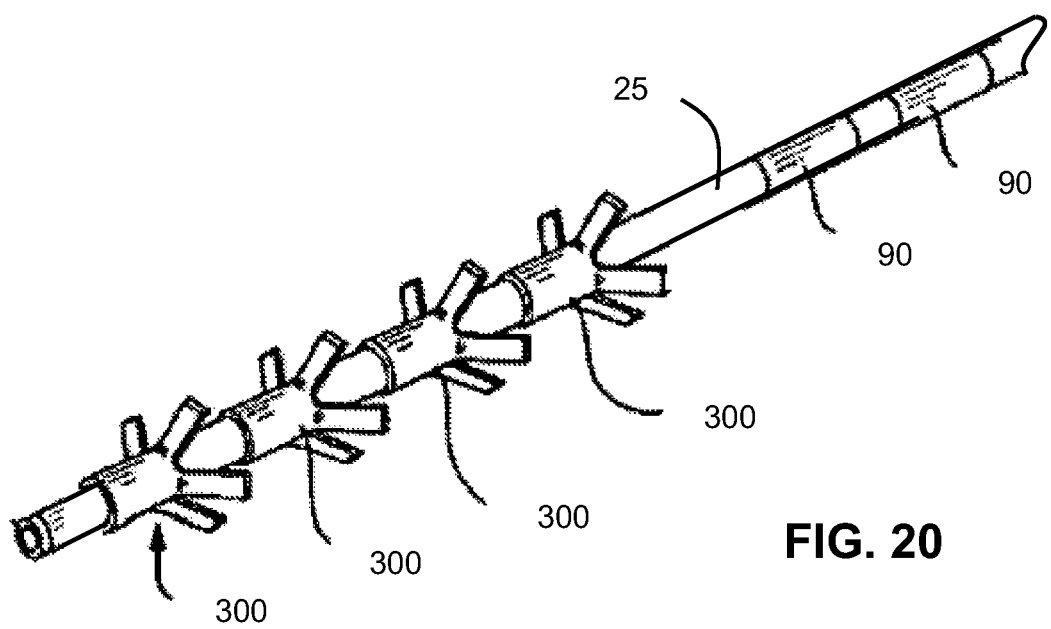
FIG. 20 is a schematic plan view of a lead with tines.

Referring now to FIG. 20, a lead 20 including tine elements 300 distal to electrodes 90 is shown. The lead 20 may have any suitable number of tine elements 300 (four in the depicted embodiment). The tine elements 300 may be associated with the lead 20 in any suitable manner. For example, one or more tine element 300 may be disposed about the lead body 25 or may be integrally formed with lead body 25. In the depicted embodiment, the tine elements 330 are disposed in proximity to the distal end of the lead 20 distal to the electrodes 90. If a tine element 330 is disposed about the lead body 25, the tine element 300 may be fixed relative to the lead body 25 via any suitable mechanism, such as crimping, adhesive, fastener, or the like. A tine element 300 may have any number of tines.

Figure 21:
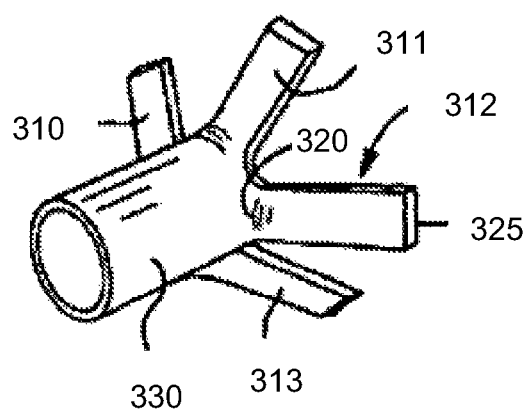
FIG. 21 is a schematic plan view of a representative tine element.

For example and referring to FIG. 21, a tine element having four tines 310, 311, 312, 313 is shown. The tine element depicted in FIG. 21 includes a mounting band 330. The mounting band 330 is configured to encircle a lead body with the tines 310, 311, 312, 313 extending from respective attached tine ends or roots disposed apart from one another around the tine mounting band 330. The tines 310, 311, 312, 313 preferably have a thickness that enables folding of the tines against the body of the lead about which they are disposed. In the depicted embodiment, the tines 310, 311, 312, 313 extend radially outward and proximally at about 45 degrees to the axis of the lead body and mounting band 330 in their relaxed and deployed state. Of course the tines may extend outwardly at nearly any suitable degree to the axis of the lead body or mounting band, if present.

It will be understood that nearly any suitable self-expanding fixation element, such as a tine element, may be employed with the teachings presented herein. Examples of other fixation elements include collapsible and expandable baskets, and the like. Any self-expanding deployable fixation element capable of introduction in a collapsed form may be employed. Such fixation elements generally are formed from or include resilient polymers, super-elastic polymers or alloys, such as nitinol, or the like.

Those skilled in the art will recognize that the preferred embodiments may be altered or amended without departing from the true spirit and scope of the disclosure, as defined in the accompanying claims.

What is claimed is:

1. A method for implanting a lead having a fixation element distal an electrode, comprising:
   providing an introducer including a body member having a proximal end and a distal end, wherein the body member defines a lumen extending from the proximal end to the distal end;
   providing a lead including:
   a lead body having a proximal end and a distal end,
   a distal electrode at or near the distal end of the lead body,
   a fixation element located between the proximal end of the lead body and the distal electrode,
   an electrode array located between the proximal end of the lead body and the fixation element,
   a first positional marking on or in the lead body located between the proximal end of the lead body and the electrode array, the first marking positioned a distance from the distal electrode equal to the distance from the proximal end of the introducer body member to the distal end of the introducer body member, and
   a second positional marking on or in the lead body located between the proximal end of the lead body and the first marking, the second marking positioned a distance from the first marking equal to (i) the distance from the distal electrode to a desired location in the electrode array, or (ii) the average distance of one or more electrodes of the electrode array from the distal electrode;
   inserting the distal end of the body member of the introducer into the patient and advancing the distal end to a location of the patient;
   inserting the lead into the lumen of the introducer until the first marking of the lead is aligned with, or adjacent to, the proximal end of the body member of the introducer, resulting in the distal electrode being extended beyond the distal end of the introducer and the fixation element being retained in a retracted position by a portion of the body member of the introducer proximal the distal end;
   applying a test electrical signal to the patient via the distal electrode to determine whether the distal electrode is in a desired location of the patient;
   advancing the lead distally through the introducer until the second marking is aligned with, or adjacent to, the proximal end of the introducer, causing the fixation element to deploy, if the distal electrode was determined to be in the desired location of the patient;
   withdrawing the introducer body member over the lead, leaving the lead implanted in the patient such that the desired location of the electrode array is positioned in the desired location of the patient.

2. A method for implanting a lead having a fixation element distal an electrode, comprising:
   providing an introducer including a body member having a proximal end and a distal end, wherein the body member defines a lumen extending from the proximal end to the distal end;
   providing a lead including:
   a lead body having a proximal end and a distal end,
   a distal electrode at or near the distal end of the lead body,
   a fixation element located between the proximal end of the lead body and the distal electrode,
   an electrode array located between the proximal end of the lead body and the fixation element,
   a first positional marking on or in the lead body located between the proximal end of the lead body and the electrode array, the first marking positioned a distance from the distal electrode equal to the distance from the proximal end of the introducer body member to the distal end of the introducer body member, and
   a second positional marking on or in the lead located between the first positional marking and the electrode array, the second marking positioned a distance from the first marking equal to (i) the distance from the distal electrode to a desired location in the electrode array, or (ii) the average distance of one or more electrodes of the electrode array from the distal electrode;
   inserting the distal end of the body member of the introducer into the patient and advancing the distal end to a location of the patient;
   inserting the lead into the lumen of the introducer until the first marking of the lead is aligned with, or adjacent to, the proximal end of the body member of the introducer, resulting in the distal electrode being extended beyond the distal end of the introducer and the fixation element being retained in a retracted position by a portion of the body member of the introducer proximal the distal end;
   applying a test electrical signal to the patient via the distal electrode to determine whether the distal electrode is in a desired location of the patient;
   advancing the introducer body member over the lead until the proximal end of the introducer body member is aligned with, or adjacent to, the second marking of the lead, if the distal electrode was determined to be in the desired location of the patient;
   advancing the lead distally through the introducer lumen until the first marking is aligned with, or adjacent to, the proximal end of the introducer;
   withdrawing the introducer body member over the lead, causing the fixation element to deploy and leaving the lead implanted in the patient such that the desired location of the electrode array is positioned in the desired location of the patient.

3. An implantable medical lead, comprising:
   a lead body having a proximal end and a distal end;
   a distal electrode at or near the distal end of the lead body configured to apply a test electrical signal to the patient to determine whether the distal electrode is in a desired location of the patient;
   a fixation element located between the proximal end of the lead body and the distal electrode, the fixation element having a proximal end and a distal end;
   an electrode array located between the proximal end of the lead body and the fixation element;
   a first positional marking located between the proximal end of the lead body and the electrode array, the first marking positioned a distance from the distal electrode equal to, or greater than, the length of an introducer sheath for use in implanting the lead; and
   a second positional marking, the second marking positioned a distance from the first marking equal to the distance from the distal electrode to a desired location in the electrode array.

4. A lead according to claim 3, wherein the second positional marking is located between the proximal end of the lead body and the first positional marking.

5. A lead according to claim 3, wherein the second positional marking is located between the first positional marking and the distal end of the lead body.

6. A lead according to claim 3, wherein the distance from the distal electrode to the desired location in the electrode array is (i) the distance from the distal electrode to an electrode of the array, or
(ii) the average distance of one or more electrodes of the electrode array from the distal electrode.

7. A lead according to claim 3, further comprising a third positional marking proximal the first positional marking, the third positional marking being located a distance from the proximal end of the fixation element equal to the length of the introducer.

8. A lead according to claim 3, further comprising:
a first contact electrically coupled to the distal electrode; and
an array of contacts, where each contact in the array of contacts is electrically coupled to a discrete electrode of the array of electrodes.

9. A lead according to claim 8, wherein the first contact and the array of contacts are positioned such that, when the lead is inserted into an implantable medical device, each of the first contact and the array of contacts is operably couplable to a discrete internal contact of an implantable medical device.

10. A lead according to claim 8, wherein the first contact and the array of contacts are positioned such that, when the lead is inserted into an implantable medical device, each of the contacts of an array of contacts is operably couplable to a discrete internal contact of the device, but the first contact is not operably couplable to a discrete internal contact of the device.

11. A lead according to claim 3, wherein the lead body defines a lumen opening to the proximal end, wherein the lumen is configured to slidably receive a stylet.

12. A lead according to claim 11, wherein the distal electrode forms a cavity in communication with the lumen of the lead, wherein the cavity is configured to receive the stylet and to electrically couple the stylet to the distal electrode.

13. A lead according to claim 12, wherein the distal electrode comprises a deflectable conductive element that extends into the cavity, the deflectable conductive element having a deflected configuration and an undeflected configuration and being biased toward the undeflected configuration, wherein, when the stylet is received in the cavity, the deflectable conductive element assumes the deflected configuration and electrically contacts the stylet.

14. A system comprising:
an introducer including a body member having a proximal end and a distal end, wherein the body member defines a lumen extending from the proximal end to the distal end; and
an implantable medical lead configured to be inserted in the lumen of the introducer, the lead including:
a lead body having a proximal end and a distal end,
a distal electrode at or near the distal end of the lead body configured to apply a test electrical signal to the patient to determine whether the distal electrode is in a desired location of the patient,
a fixation element located between the proximal end of the lead body and the distal electrode,
an electrode array located between the proximal end of the lead body and the fixation element,
a first positional marking located between the proximal end of the lead body and the electrode array, the first marking positioned a distance from the distal electrode equal to, or greater than, the length of an introducer sheath for use in implanting the lead, and
a second positional marking, the second marking positioned a distance from the first marking equal to the distance from the distal electrode to a desired location in the electrode array.

15. A system according to claim 14, wherein the second positional marking is located between the first positional marking and the distal end of the lead body.

16. A system according to claim 14, wherein the second positional marking is located between the first positional marking and the proximal end of the lead body.

17. A system according to claim 14, wherein the distance from the distal electrode to the desired location in the electrode array is (i) the distance from the distal electrode to an electrode of the array, or (ii) the average distance of one or more electrodes of the electrode array from the distal electrode.

18. A system according to claim 14, further comprising a third positional marking located between the proximal end of the lead body and the first positional marking, the third positional marking being located a distance from the proximal end of the fixation element equal to the distance of the introducer.

19. A system according to claim 14, wherein the lead body defines a lumen opening to the proximal end, wherein the lumen is configured to slidably receive a stylet.

20. A system according to claim 19, wherein the distal electrode forms a cavity in communication with the lumen of the lead, wherein the cavity is configured to receive the stylet and to electrically couple the stylet to the distal electrode.

21. A lead according to claim 20, wherein the distal electrode comprises a deflectable contact that extends into the cavity, the deflectable contact having a deflected configuration and an undeflected configuration and being biased toward the undeflected configuration, wherein, when the stylet is received in the cavity, the deflectable contacts assume the deflected configuration and electrically contact the stylet.

22. A system according to claim 19, further comprising the stylet.

23. The method of claim 1, wherein the distal electrode is a tip electrode.

24. The method of claim 2, wherein the distal electrode is a tip electrode.

25. The lead of claim 3, wherein the distal electrode is a tip electrode.

26. The system of claim 14, wherein the distal electrode is a tip electrode.

* * * * *